(12) United States Patent
Oka et al.

(10) Patent No.: US 9,714,886 B2
(45) Date of Patent: Jul. 25, 2017

(54) SAMPLE INJECTION DEVICE FOR BIOCHEMICAL ANALYSIS, FLOW-TYPE BIOCHEMICAL ANALYSIS DEVICE, AND MEASUREMENT METHOD FOR HEMOGLOBIN COMPONENT

(71) Applicant: Sekisui Medical Co., Ltd., Tokyo (JP)

(72) Inventors: Takayuki Oka, Tokyo (JP); Takuya Yotani, Tokyo (JP); Hideki Muraki, Tokyo (JP)

(73) Assignee: Sekisui Medical Co., Ltd. (JP)

( * ) Notice: Subject to any disclaimer, the term of this patent is extended or adjusted under 35 U.S.C. 154(b) by 14 days.

(21) Appl. No.: 14/357,274

(22) PCT Filed: Nov. 9, 2012

(86) PCT No.: PCT/JP2012/079125
§ 371 (c)(1),
(2) Date: May 9, 2014

(87) PCT Pub. No.: WO2013/069769
PCT Pub. Date: May 16, 2013

(65) Prior Publication Data
US 2014/0287453 A1 Sep. 25, 2014

(30) Foreign Application Priority Data

Nov. 11, 2011 (JP) ................. 2011-247647

(51) Int. Cl.
*G01N 1/18* (2006.01)
*G01N 30/24* (2006.01)
(Continued)

(52) U.S. Cl.
CPC ............... *G01N 1/14* (2013.01); *G01N 30/18* (2013.01); *G01N 30/20* (2013.01); *G01N 2030/8822* (2013.01)

(58) Field of Classification Search
CPC .......... G01N 1/14; G01N 30/18; G01N 30/20; G01N 2030/8822
See application file for complete search history.

(56) References Cited

U.S. PATENT DOCUMENTS 5,431,067 A * 7/1995 Anderson ............ G01N 1/2035
73/863.86
2011/0189713 A1 * 8/2011 Le Comte ................ G01N 1/38
435/29

FOREIGN PATENT DOCUMENTS

EP 0141148 A1 5/1985
EP 1275957 A2 1/2003
(Continued)

OTHER PUBLICATIONS

Extended European Search Report for Application No. 12848233.8 dated Aug. 13, 2015.
(Continued)

*Primary Examiner* — Robert Eom
(74) *Attorney, Agent, or Firm* — Lerner, David, Littenberg, Krumholz & Mentlik, LLP

(57) ABSTRACT

When injecting a sample into carrier-liquid channels (3A and 3B), injection shock is prevented. Septa 13 and 14 constitute the upper wall and the lower wall of a sample injection part (11) of the carrier-liquid channels (3A and 3B). A needle (27) can vertically penetrate the septum (13) on the upper wall side and also penetrate the septum (14) on the lower wall side. A needle moving unit (28) induces the needle (27) to penetrate the septum (14) on the lower wall side and induces the tip of the needle to face the inside of a sample vessel (26). A measurement pump (29) is operated for drawing and as a result a sample is drawn into the needle (27). Next, the needle (27) is extracted from the septum (14) on the lower wall side, the tip of the needle is induced to face the inside of the sample injection part (11), the measurement
(Continued)

US 9,714,886 B2

Page 2 pump (29) is caused to discharge and as a result the sample within the needle (27) is injected.

4 Claims, 6 Drawing Sheets

(51) Int. Cl.
*G01N 1/14* (2006.01)
*G01N 30/18* (2006.01)
G01N 30/88 (2006.01)
G01N 30/20 (2006.01)

(56) References Cited

FOREIGN PATENT DOCUMENTS

| | | |
|---|---|---|
| JP | 57066358 | 4/1982 |
| JP | 63084562 | 6/1988 |
| JP | 05256834 | 10/1993 |
| JP | 2011013045 A | 1/2011 |
| WO | 2011085285 A1 | 7/2011 |

OTHER PUBLICATIONS

International Search Report for Application No. PCT/JP2012/079125 dated Feb. 19, 2013.

* cited by examiner

SAMPLE INJECTION DEVICE FOR BIOCHEMICAL ANALYSIS, FLOW-TYPE BIOCHEMICAL ANALYSIS DEVICE, AND MEASUREMENT METHOD FOR HEMOGLOBIN COMPONENT

TECHNICAL FIELD

The present invention relates to a sample injection device for biochemical analysis for excellently injecting a sample into a carrier-liquid channel, and further relates to a flow-type biochemical analysis device which uses the sample injection device, and to a measurement method for hemoglobin components, such as hemoglobin A1c.

BACKGROUND ART

As a conventional sample injection device for biochemical analysis of this type, the device disclosed in Patent Document 1 is known. In this device, a sample injection valve is provided in a carrier-liquid (eluant) channel which allows the carrier liquid to flow into a column by means of a pump, and the valve has a sample drawing position and a sample injection position.

In addition, it is necessary to wash the needle each time a new sample is drawn, and a needle washing unit for the washing is separately provided.

At the sample drawing position, the upper flow channel and the lower flow channel of the carrier-liquid channel are connected as a short circuit, and on the other hand, the sample loop is separated from the carrier-liquid channel, and the sample is drawn into the sample loop in this state.

At the sample injection position, the upper flow channel and the lower flow channel of the carrier-liquid channel are connected via the sample loop, and thereby the sample is injected into the flow of the carrier liquid.

In addition, after the sample is injected, the needle is moved to a needle washing position, which is separately provided, to undergo washing.

CITATION LIST

Patent Document

[Patent Document 1] Japanese Laid-Open Patent Application No. H05-256834

SUMMARY OF THE INVENTION

Problems to be Solved by the Invention

However, in the conventional sample injection device, in shifting from the sample drawing position to the sample injection position, the carrier-liquid channel is temporarily blocked, and therefore the flow of the carrier liquid is disturbed. In addition, when the sample loop is connected to the carrier-liquid channel, the flow rate is changed due to pressure fluctuation because the pressure in the carrier-liquid channel is high while the inside of the sample loop is at atmospheric pressure, and this change of the flow rate also causes disturbance in the flow. Thus, a phenomenon known as injection shock may occur, which adversely affects the analysis.

Note that in the device disclosed in Patent Document 1, shifting between constant flow rate control and constant pressure control is carried out to prevent injection shock, however, it is difficult to carry out the control with a high precision due to response lags in the control and the like, and this is considered to at least interrupt an increase in the speed of analyses.

In the conventional sample injection device, a washing position is separately provided for washing of the needle carried out after a sample is injected, and because a large area for installing a washing unit and a large amount of washing liquid are necessary to increase the washing efficiency, it becomes difficult to downsize the device and to maintain the washing efficiency.

In consideration of the above situation, the purpose of the invention is to provide a sample injection device for biochemical analysis capable of excellently injecting a sample into a flow of a carrier liquid, without producing injection shocks.

Means for Solving the Problems

In order to solve the above-described problems, according to an aspect of the invention, a sample injection device is configured to include: septa that constitute an upper wall and a lower wall at a sample injection position of a carrier-liquid channel; a vessel which is arranged below the septum on the lower wall side and configured to store the sample; a cylindrical needle which penetrates through the septum on the upper wall side in a vertical direction and which is capable of further penetrating through the septum on the lower wall side; a needle moving unit configured to move the needle in a vertical direction and capable of moving the needle at least to a sample drawing position, at which a tip of the needle penetrates through the septum on the lower wall side to face an inside of the vessel, and to a sample injection position, at which the tip of the needle exits through the septum on the lower wall side to face an inside of the carrier-liquid channel; and a measurement pump connected with the needle on a side of a base end section thereof and configured to carry out drawing when the needle is positioned at the sample drawing position and carry out discharge when the needle is positioned at the sample injection position.

In addition, it is preferable that a washing position be set at an intermediate position between the sample drawing position and the sample injection position by the use of the needle moving unit, and a washing mechanism configured to wash the tip of the needle is arranged at the washing position.

In addition, according to an aspect of the invention, a flow type biochemical analysis device is configured to include the sample injection device described above; and a separation and detection unit provided in a carrier-liquid channel on a downstream side of the sample injection device and configured to separate and detect a content in the sample.

Furthermore, the flow type biochemical analysis device can be preferably used for measuring hemoglobin components (in particular, hemoglobin A1c) in diabetes testing. Accordingly, in a measurement method for hemoglobin components according to an aspect of the present invention, blood is injected into the carrier-liquid channel as the sample using the above sample injection device; and hemoglobin components contained in the blood are separated and detected and the amount of the components (hemoglobin A1c and the like) is measured. Note that in this specification, the term "blood" used for measurement of hemoglobin components refers to a sample containing red blood cells, such as whole blood, whole blood diluted with a buffer solution or the like, a red blood cell fraction obtained by natural precipitation or centrifugal separation, washed red blood cells, and the like.

Effects of the Invention

In the sample injection device according to an aspect of the present invention, the needle is induced to penetrate through the septum on the lower wall side and to move to the sample drawing position, then a sample is drawn, then the needle is extracted from the septum on the lower wall side and induced to move to the sample injection position, and thus the sample can be injected.

Because the configuration which uses the septa as described above is employed, the carrier-liquid channel is not blocked when the sample is injected, and accordingly, no injection shock may occur, and as a result, the sample can be preferably injected into the constant flow of the carrier liquid. Furthermore, because the configuration which uses the septa is employed, conventional sample injection valves, and the like become unnecessary, and therefore a small device can be configured at low costs, and it is possible to easily carry out a maintenance operation.

In addition, with a needle washing mechanism provided at an intermediate position between the sample drawing position and the sample injection position between which the needle is vertically moved, which mechanism being integrated to the mechanism of the sample injection device, the sample injection device can have a configuration which does not require an installation area for a separate washing unit. Furthermore, the inside of the needle is washed with the washing liquid when the needle is washed; the outside of the needle is washed by drawing a mist-like mixture of the washing liquid and air by using the discharge pump after preparing the mist-like mixture; and thus, the washing efficiency is increased, and thereby the volume of the washing liquid to be consumed can be reduced, which thereby enables preferable washing of the needle.

Therefore, according to the flow type biochemical analysis device having a configuration which uses the sample injection device described above, it is possible to carry out a highly precise analysis at high speed while contributing to downsizing of the device.

In addition, by measuring hemoglobin components (in particular, hemoglobin A1c) contained in blood by liquid chromatography by using the sample injection device described above, it is possible to carry out the measurement with high precision and at high speed.

MODE FOR CARRYING OUT THE INVENTION

Figure 1:
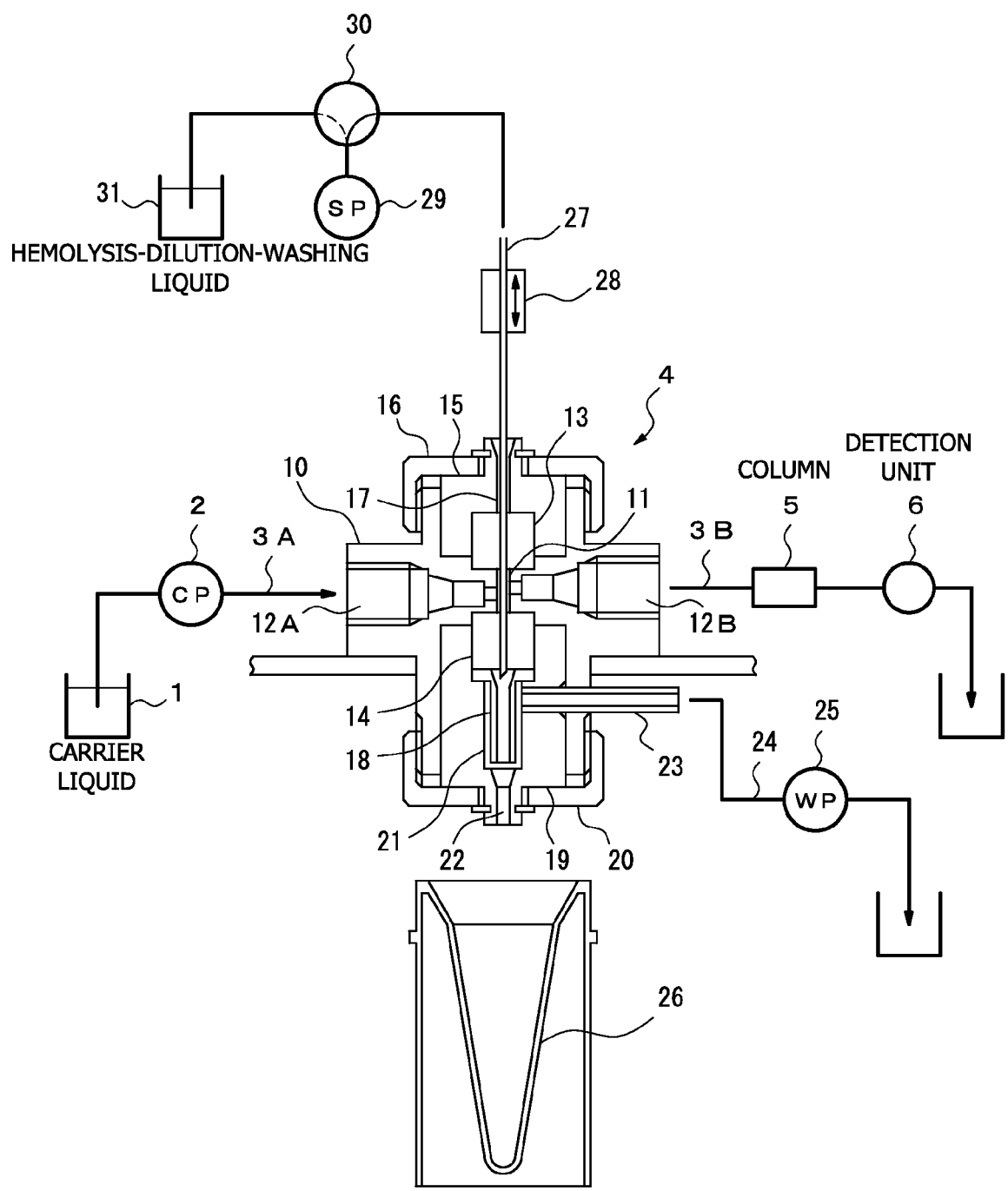
FIG. 1 is a system view illustrating an embodiment of a flow type biochemical analysis device including a sample injection device according to the present invention.

An embodiment of the invention will be described below. FIG. 1 is a system view illustrating an embodiment of a flow type biochemical analysis device including a sample injection device according to the present invention.

The flow type biochemical analysis device according to the present embodiment is used to analyze respective hemoglobin components included in blood, such as hemoglobin A1c, based on the principle of high-performance liquid chromatography (HPLC). Accordingly, the sample is blood. In addition, hemolysis treatment is necessary as pretreatment and hemolysis liquid is used, and hemolysis-dilution-washing liquid, which is used for multiple purposes of hemolysis, dilution, and washing, is used as the hemolysis liquid.

A flow type biochemical analysis device illustrated in FIG. 1 includes a carrier pump 2, which is configured to continuously feed a carrier liquid from a carrier liquid tank 1; carrier-liquid channels 3A and 3B for feeding the carrier liquid from the carrier pump 2; a sample injection device 4 arranged in the carrier-liquid channels 3A and 3B; a column 5 which is arranged on the downstream side of the sample injection device 4 and configured to separate a component contained in a sample; and a detection unit 6, which is arranged on the downstream side of the column 5 and configured to detect the separated component and transmit a signal thereof to a data processing apparatus (not illustrated). Results of the data processing by the data processing apparatus are output as analysis results.

Figure 6:
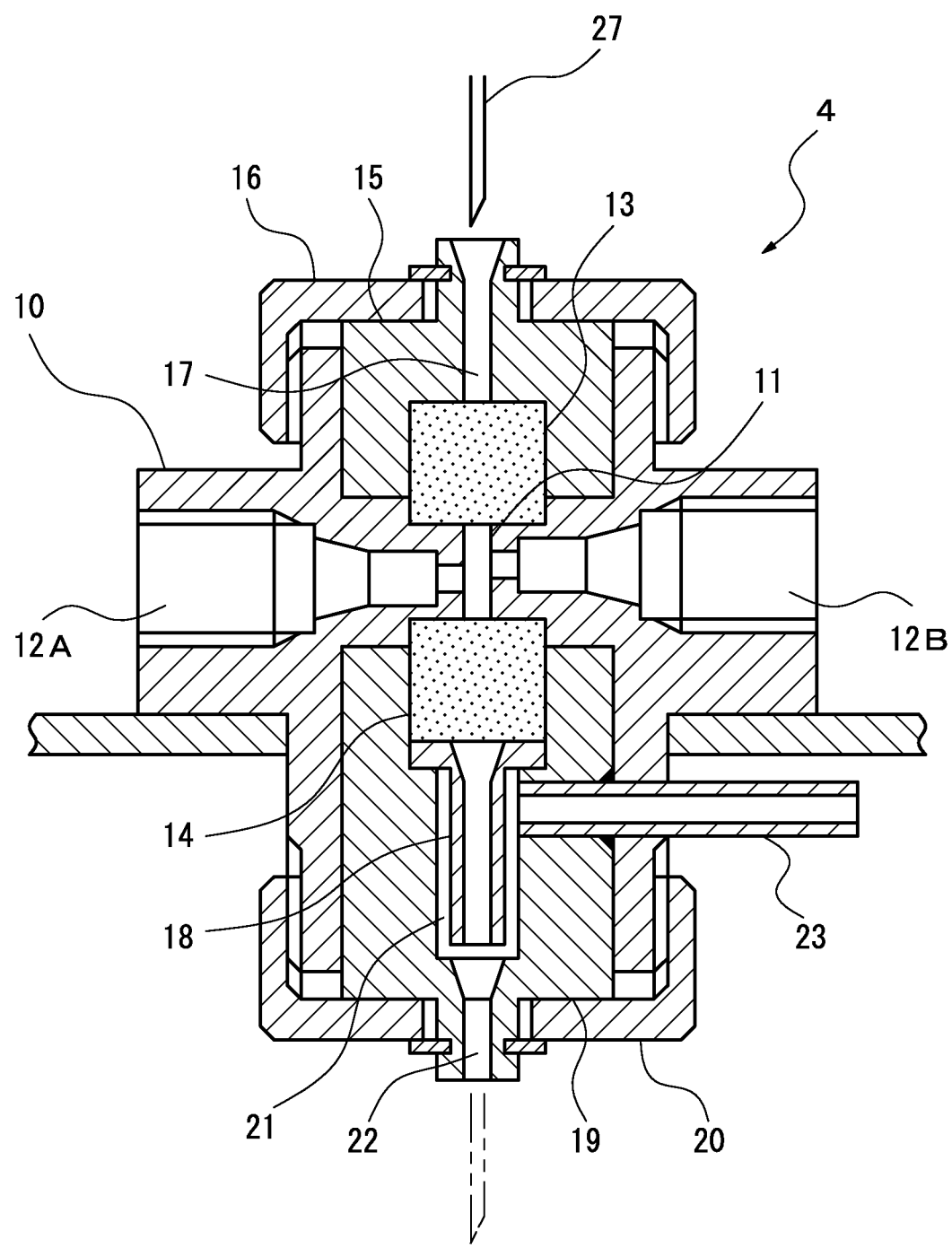
FIG. 6 is an enlarged cross sectional view of a main part of the sample injection device.

The sample injection device 4 will be described in detail with reference to FIGS. 1 and 6. FIG. 6 is an enlarged cross sectional view of a main part of the sample injection device 4 illustrated in FIG. 1 and illustrates a state before a needle 27, which will be described below, is set.

The sample injection device 4 primarily includes a housing 10, and the following are formed on the housing 10: a sample injection part 11, which is formed in a vertically penetrating manner; an inlet-side channel 12A extending in a horizontal direction from a side wall opening part, which is a junction with the channel 3A on the side of the carrier pump 2, and opening to the sample injection part 11; and an outlet-side channel 12B extending in a horizontal direction from a side wall opening part, which is a junction with the channel 3B on the side of the column 5, and opening to the sample injection part 11.

An upper end side of the sample injection part 11 is stopped up with a septum 13 and a lower end side of the sample injection part 11 is stopped by another septum 14. Note that the septa 13 and 14 are constituted by silicone rubber and the like, and if it is penetrated by a needle, the hole is closed by its own elasticity to maintain its airtight and liquidtight state.

Accordingly, the carrier liquid fed by the carrier pump 2 enters the sample injection part 11 from the inlet-side channel 12A, and then is allowed to flow from the sample injection part 11 toward the column 5 via the outlet-side channel 12B. The septum 13, which stops up the upper-end side of the sample injection part 11, constitutes the upper wall of a sample injection position of the carrier-liquid channel, and the septum 14, which stops up the lower-end side of the sample injection part 11, constitutes the lower wall of the sample injection position of the carrier-liquid channel.

The openings of the inlet-side channel 12A and the outlet-side channel 12B of the sample injection part 11 are vertically offset from one another, and thereby retention of the carrier liquid in the sample injection part 11 is prevented as much as possible.

The septum 13, which stops the upper end side of the sample injection part 11, is sandwiched between the housing 10 and an upper block 15, and the upper block 15 is fixed by a locking nut 16. The upper block 15 includes a guide hole 17, which extends in a vertical direction on a line extended from the sample injection part 11.

The septum 14, which stops the lower end side of the sample injection part 11, is sandwiched between the housing 10 and a lower block 19 together with a flange part of a cylindrical guide 18 arranged below the septum 14, and the lower block 19 is fixed by a locking nut 20.

The hole on the side of the inner periphery of the cylindrical guide 18 is arranged in the vertical direction on a line extended from the sample injection part 11. The lower block 19 has an annular space 21, which is formed so as to surround an outer periphery of the cylindrical guide 18 including a tip thereof, and the lower block 19 further has a guide hole 22, which is in communication with the annular space 21 and extends in a vertical direction on a line extended from the sample injection part 11 (i.e., on a line extended from the hole on the side of the inner periphery of the cylindrical guide 18).

One end of a discharge pipe 23 opens in a relatively upper part of the annular space 21 of the lower block 19, and the other end of the pipe 23 penetrates through the housing 10 and opens toward the outside. In addition, a discharge path 24 is connected to the other end of the pipe 23, and a discharge pump 25 (or a waste pump 25) is provided in the discharge path 24.

A sample vessel 26 is arranged below the housing 10 of the sample injection device 4, more specifically, below the guide hole 22. This vessel 26 also serves as a vessel for hemolysis and dilution of the sample. Note that with respect to the sample injection device 4, the device shall include a configuration in which the vessel 26 can be positioned and set; however, a feeding mechanism can be included.

The guide hole 17, the sample injection part 11, the cylindrical guide 18 (the hole on the side of the inner periphery thereof), and the guide hole 22 are arranged on a straight line in the vertical direction to form a moving path for the needle 27. The septa 13 and 14 are arranged above and below the sample injection part 11, respectively on the above-described straight line, and the needle 27 can penetrate therethrough in an airtight and liquidtight manner. In addition, the sample vessel 26 is arranged on an extension of the straight line, and thus the needle 27 can face the sample vessel 26.

The needle (nozzle) 27 is formed so as to have a long cylindrical shape (a shape of an injection needle) with the tip on the lower end side as a sharp needle tip.

Accordingly, the needle 27 can be caused to penetrate through the upper septum 13 from the guide hole 17 so that the tip can face the sample injection part 11, and can be further caused to penetrate through the lower septum 14 so that the tip can face the inside of the cylindrical guide 18. Furthermore, the needle 27 can be inserted through the guide hole 22 from the cylindrical guide 18 so that the tip can be exposed to the outside and face the inside of the sample vessel 26.

In addition, a needle moving unit 28 capable of inducing the needle 27 to move in the vertical direction is equipped with the needle 27.

The needle moving unit 28 is capable of inducing the needle 27 to move in the vertical direction at least to the sample drawing position, at which the tip of the needle 27 faces the inside of the sample vessel 26 after penetrated through the lower septum 14, and to the sample injection position, at which the tip of the needle 27 faces the inside of the carrier-liquid channel (the sample injection part 11) after extracted from the lower septum 14. Note that the needle moving unit 28 can be configured to include a progressive step motor or the like, which converts a rotational motion of a rotor (nut) into translatory movement of a non-rotational shaft (screw).

The needle 27 is connected with a measurement pump (sampling pump) 29 at a base end section thereof on the upper end side via a switching valve 30, which will be described below. Accordingly, by operating the measurement pump 29 to draw the sample, the sample can be drawn into the inside of the needle 27 from the tip side thereof, and then by operating the measurement pump 29 to discharge the sample, the sample that has been drawn into the inside of the needle 27 can be discharged from the tip thereof.

In addition, the measurement pump 29 can be connected selectively with the base end section of the needle 27 and with the hemolysis-dilution-washing liquid tank 31 via the switching valve 30. In other words, the switching valve 30 is a three-way valve and connects the measurement pump 29 and the hemolysis-dilution-washing liquid tank 31 at one position and the measurement pump 29 and the needle 27 at the other position. Accordingly, the measurement pump 29 is capable of discharging the hemolysis-dilution-washing liquid drawn from the liquid tank 31 at one position of the switch valve 30 toward the side of the needle 27 at the other position of the switching valve 30.

Next, a series of operations of the above-described sample injection device 4 will be described with reference to a case of measuring hemoglobin A1c in blood, which is carried out in diabetes testing.

S1: Feeding of a carrier liquid by the carrier pump 2 is started to fill the carrier-liquid channels 3A and 3B including the sample injection part 11, the column 5, and the detection unit 6 with the carrier liquid.

Subsequently, washing steps before sample drawing are carried out (S2 to S5).

S2: The switching valve 30 is switched to a position for connecting the measurement pump 29 and the hemolysis-dilution-washing liquid tank 31 to measure and draw the hemolysis-dilution-washing liquid (the washing liquid) by using the measurement pump 29. After the drawing is completed, the switching valve 30 is switched to a position for connecting the measurement pump 29 and the needle 27.

S3: The discharge pump 25 is turned ON.

S4: The measurement pump 29 is caused to discharge, and the washing liquid is fed to the needle 27 to wash the inside of the needle 27 and the inside and the outside of cylindrical guide 18.

In this step, as illustrated in FIG. 1, the needle 27 is positioned at a washing position, at which the tip has penetrated through the lower septum 14 to face the upper part inside the cylindrical guide 18. In addition, because the flow rate of the discharge pump 25 is higher than the flow rate of the measurement pump 29, after the washing is completed, the washing liquid is discharged by the discharge pump 25 from the annular space 21 via the pipe 23 together with the air entered from the guide hole 22.

Figure 2:
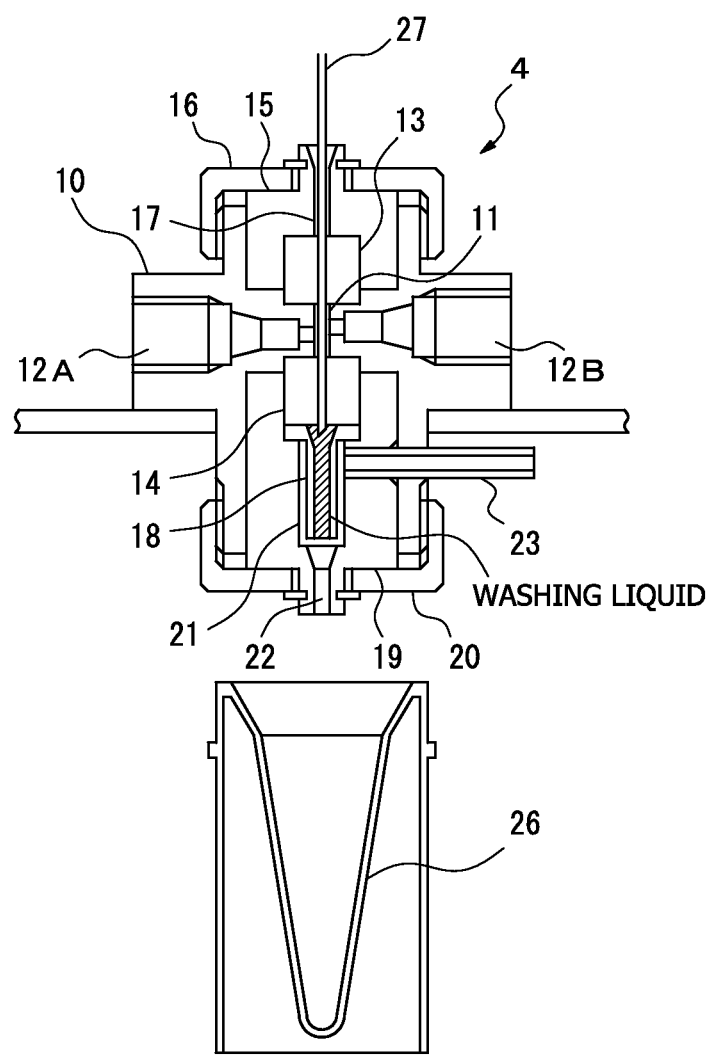
FIG. 2 is a drawing illustrating a state of the sample injection device when a needle is positioned at a washing position.

S5: The discharge pump 25 is turned OFF. In this step, the inner periphery side of the cylindrical guide 18 is filled with the residual washing liquid as illustrated in FIG. 2 as a shaded portion.

Subsequently, sample hemolysis-dilution steps are performed (S6 to S12).

S6: The switching valve 30 is switched to the position connecting to the tank 31 and the hemolysis-dilution-washing liquid (hemolysis and dilution liquid) is measured and drawn by using the measurement pump 29. After the drawing is completed, the switching valve 30 is switched to the position connecting to the needle 27.

Figure 3:
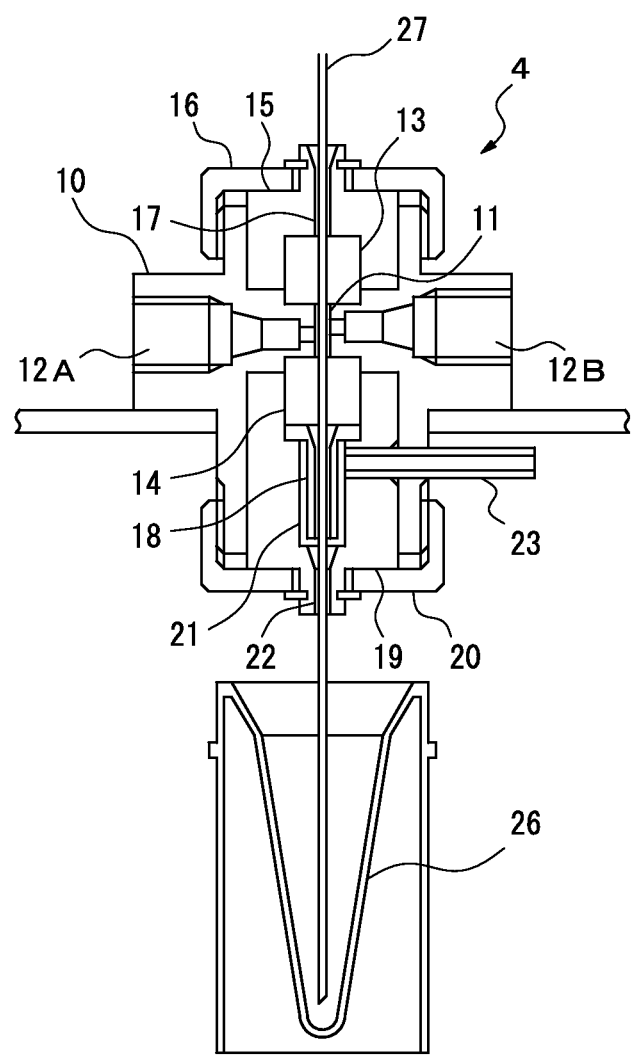
FIG. 3 is a view illustrating a state of the sample injection device when the needle is positioned at a sample drawing position.

S7: The needle moving unit 28 causes the needle 27 to move down to the lowermost position as illustrated in FIG. 3, at which the tip of the needle 27 faces the inside of the vessel 26 (i.e., at the same position as the sample drawing position).

S8: The measurement pump 29 is caused to discharge, the hemolysis and dilution liquid is fed to the needle 27, and allowed to enter the inside of the vessel 26 from the tip of the needle 27.

S9: A separately measured sample (blood for testing) is transferred manually or automatically into the inside of the vessel 26. Note that the filling of the separately measured sample (blood for testing) into the inside of the vessel 26 is not limited to filling carried out after S8, i.e., the filling of the separately measured sample can be previously carried out prior to S8.

Figure 4:
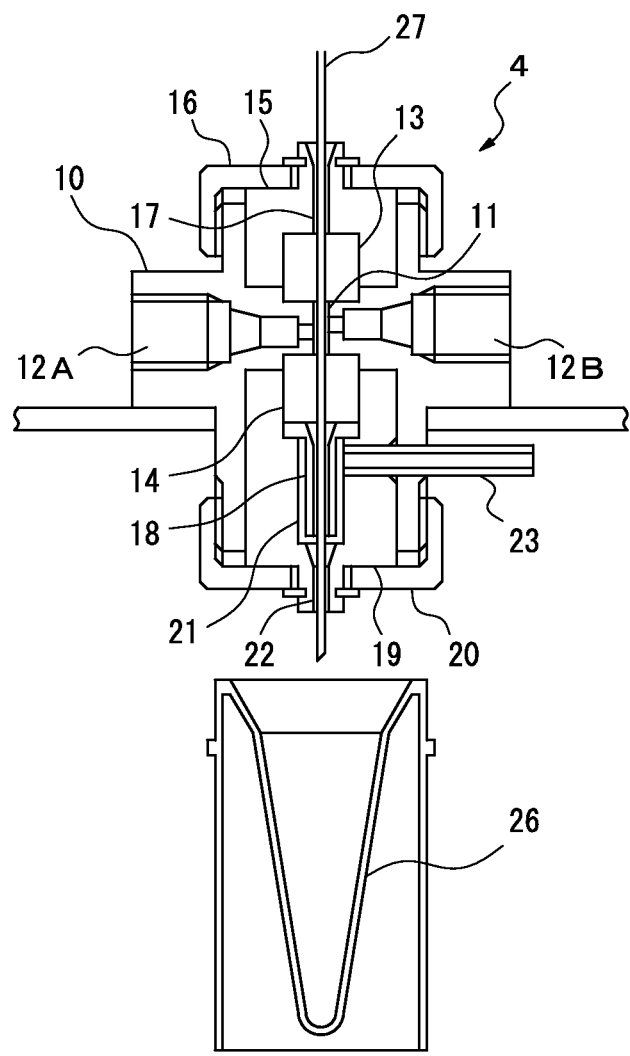
FIG. 4 is a view illustrating a state of the sample injection device when the needle is positioned at a partitioning air drawing position.

S10: The needle moving unit 28 causes the needle 27 to move upward off the level of the liquid in the inside of the vessel 26 as illustrated in FIG. 4 so that the tip of the needle 27 is positioned at a position at which air can be drawn. Then, the measurement pump 29 is caused to draw the drawing partitioning air to the inside of the needle 27. The partitioning air is used for preventing diffusion of the dilution liquid remaining inside the needle 27 and the dilution sample to be subsequently drawn for stirring at the boundary.

S11: The needle moving unit 28 causes the needle 27 to move down again to the lowermost position, as illustrated in FIG. 3.

S12: The measurement pump 29 is operated to repeatedly carry out drawing and discharge operations to draw and discharge a liquid mixture of the sample and the hemolysis and dilution liquid inside the vessel 26 by using the needle 27, and thereby the liquid mixture inside the vessel 26 is stirred and the sample is uniformly hemolyzed and diluted. Finally, the measurement pump 29 carries out a discharge operation to discharge the partitioning air. This is carried out to prevent the partitioning air from entering the analysis line in the subsequent sample injection step, thereby preventing noise.

Next, sample drawing and injection steps are carried out (S13 to S16).

S13: The measurement pump 29 is operated to measure and draw the sample at the sample drawing position illustrated in FIG. 3, and thereby the hemolyzed and diluted sample is drawn from the inside of the vessel 26 into the inside of the needle 27. In this step, the amount to be drawn is larger than the amount of injection into the analysis line (larger than the total injection amount if the same sample is injected multiple times).

Figure 5:
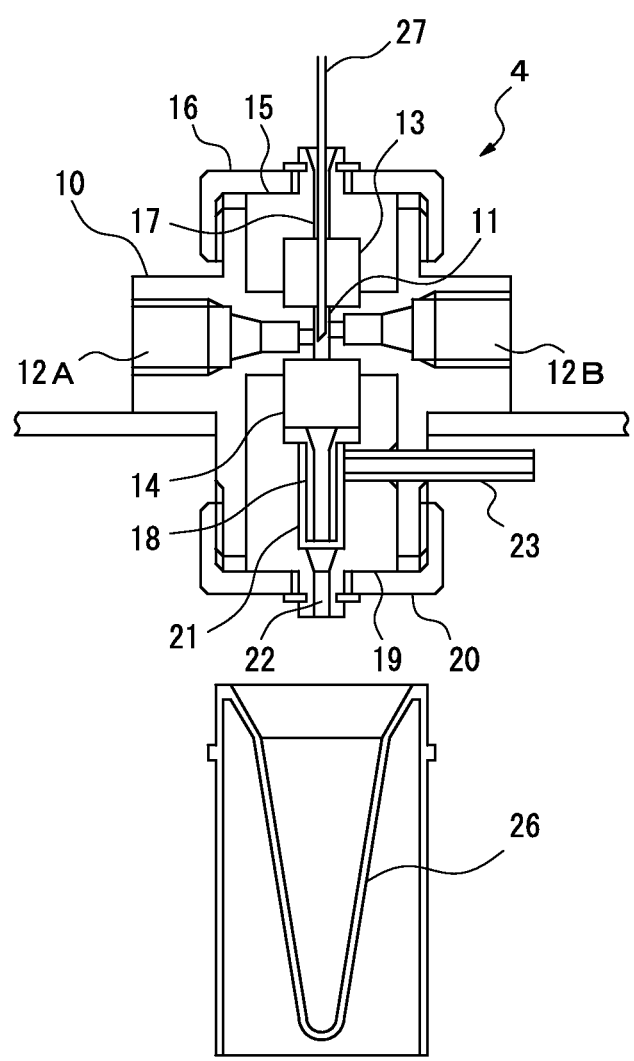
FIG. 5 is a view illustrating a state of the sample injection device when the needle is positioned at a sample injection position.

S14: The needle moving unit 28 causes the needle 27 to move up to the sample injection position as illustrated in FIG. 5, at which the tip of the needle 27 faces the carrier-liquid channel (the sample injection part 11). Subsequently, the measurement pump 29 is operated for discharge to inject a predetermined amount of hemolyzed and diluted sample into the flow of the carrier liquid.

S15: The needle moving unit 28 induces the needle 27 to move to the washing position illustrated in FIG. 2. In the course of the movement, contaminants from the sample that has adhered to the outside of the needle 27 are squeezed and removed by the lower septum 14 and washed off with the washing liquid filling the inside of the cylindrical guide 18.

S16: The injected sample is separated by the column 5 on the downstream side, and the separated component is detected by the detection unit 6.

If the same sample is to be analyzed again, the following steps are carried out (S17 to S20).

S17: The needle moving unit 28 induces the needle 27 to move up to the sample injection position as illustrated in FIG. 5. Then the measurement pump 29 is operated for discharge to inject a predetermined amount of sample, of the remainder of the sample drawn in the last operation, into the flow of the carrier liquid.

S18: The needle moving unit 28 induces the needle 27 to move to the washing position illustrated in FIG. 2.

S19: The injected sample is separated by the column 5 on the downstream side, and the separated component is detected by the detection unit 6.

S20: The above-described operations in S17 to S19 can be executed multiple times.

Next, washing steps after the sample injection are carried out (S21 to S25).

S21: The discharge pump 25 is turned ON.

S22: The measurement pump 29 is operated for discharge at the washing position illustrated in FIG. 2 to dispose of the sample remaining in the inside of the needle 27.

S23: The switching valve 30 is switched to the position connecting to the tank 31 and the hemolysis-dilution-washing liquid (washing liquid) is measured and drawn by the measurement pump 29. After the drawing is completed, the switching valve 30 is switched to the position connecting to the needle 27.

S24: The measurement pump 29 is operated for discharge to feed the washing liquid to the needle 27 and wash the inside of the needle 27 and the inside and the outside of the cylindrical guide 18. In this step, the contaminated liquid remaining inside the cylindrical guide 18 used for the washing in S15 (and S18) is also disposed of.

S25: The discharge pump 25 is turned OFF.

A next sample is analyzed in the following manner.

S26: In analyzing the next sample, S6 to S25 are repeated.

The sample injection device according to the present embodiment is configured to include the septa 13 and 14, which constitute the upper wall and the lower wall at the sample injection positions of the carrier-liquid channel 3A and 3B; the vessel 26 arranged below the septum 14 on the lower wall side and in which the sample is contained; the cylindrical needle 27 which has penetrated through the septum 13 on the upper wall side in the vertical direction and which can further penetrate through the septum 14 on the lower wall side; the needle moving unit 28 which is capable of inducing the needle 27 to move in the vertical direction at least to the sample drawing position, at which the tip of the needle 27 faces the inside of the vessel 26 after having penetrated through the septum 14 on the lower wall side, and to the sample injection position, at which the tip of the needle 27 faces the inside of the carrier-liquid channel (the sample injection part 11) after having exited through the lower septum 14 on the lower wall side; and the measurement pump 29, which is connected with the needle 27 on the side of the base end section and carries out drawing when the needle 27 is positioned at the sample drawing position and discharge when the needle 27 is positioned at the sample injection position. Accordingly, the carrier-liquid channel is not blocked when the sample is injected; which enables to eliminate the occurrence of sample injection shocks, thereby achieving an analysis with a high precision.

In addition, the sample of an amount large enough for multiple analyses can be drawn, stored in a state in which it is not exposed to air, and injected into the analysis line by an amount necessary for the analysis, and accordingly, the reproducibility becomes high in analyzing the same sample multiple times.

Because the configuration which uses the septa 13 and 14 is employed, the present embodiment has advantages such that conventional sample injection valves and the like become unnecessary, that downsizing and price reduction of the device can be achieved, and that complicated maintenance operations required for conventional sample injection valves are not required.

Note that because the needle 27 always penetrates through the upper septum 13, the septum 13 can have a general sealed configuration (using an O-ring or the like); however, the configuration of the device can be simplified by employing the same configuration for the upper septum 13 as that of the septum 14 on the lower wall side.

In addition, according to the present embodiment, the measurement pump 29 can be connected selectively with the base end section of the needle 27 and the pretreatment- (hemolysis-), dilution-, or washing-liquid tank 31 via the switching valve 30, and thus the liquid drawn from the tank 31 at one position of the switching valve 30 can be discharged to the needle 27 at the other position of the switching valve 30. Accordingly, the sample injection device of the present invention can easily feed a liquid for pretreatment, dilution, or washing, and have high practicality in use.

In addition, according to the present embodiment, the device of the present embodiment is configured to further include the cylindrical guide 18 which is arranged below the lower septum 14 and guides the needle 27, and the discharge pump 25 which is connected to the space 21 surrounding the tip of the cylindrical guide 18 and capable of carrying out discharge. The device is also configured so that the needle moving unit 28 may move the needle 27 to induce the tip thereof to move to the washing position, which is inside the cylindrical guide 18 and set between the sample drawing position and the sample injection position. Further, in this configuration, the washing liquid is discharged from the tip of the needle 27 at the washing position, and thereafter drained by the use of the discharge pump 25. Accordingly, the inside and the outside of the needle 27 can be securely washed before and after the sample drawing and injection steps, and in addition, the amount of carryover becomes small because the outer periphery of the needle 27 is squeezed by the septum 14. Furthermore, the amount of the washing liquid to be used can be reduced, thus the maintenance operation of the device can be carried out at low cost, and the time for the maintenance of the device can be saved.

In other words, in the present embodiment, with a needle washing mechanism provided at an intermediate position between the sample drawing position and the sample injection position between which the needle 27 (the tip thereof) moves in the vertical direction, which mechanism being integrated to the mechanism of the sample injection device 4; the sample injection device 4 can have a configuration which does not require an installation area for a separate washing unit. Furthermore, the efficacy of needle washing is enhanced by washing the inside of the needle 27 with the washing liquid, and the outside of the needle 27 with a mist-like mixture of the washing liquid and air by drawing it by using the discharge pump 25, and thereby the volume of the washing liquid to be consumed can be reduced, which thus enables preferable washing of the needle 27.

In addition, according to the present embodiment, because the pretreatment (hemolysis) or dilution liquid can be discharged from the tip of the needle 27 to the inside of the vessel 26 at the sample drawing position, the pretreatment (hemolysis) and the dilution can be easily carried out, and as a result, the practicability becomes high.

In addition, the flow type biochemical analysis device according to the present embodiment is configured to include the sample injection device 4 described above; and the separation detection devices (the column 5 and the detection unit 6) that are provided in the carrier-liquid channel on the downstream side of the sample injection device 4 and that separate and detect components contained in the sample, and thereby any adverse effects to the analysis that may otherwise occur due to injection shock is prevented, and as a result, it is possible to carry out a highly precise analysis at a high speed.

In addition, the measurement method for hemoglobin components according to the present embodiment uses the above-described sample injection device 4 to inject blood into the carrier-liquid channel as the sample, and separates and detects the hemoglobin component contained in the blood and measures the amount of the component (hemoglobin A1c and the like); thereby the method being capable of contributing to improving the precision and the speed of diabetes testing. Note that a publicly known method can be used as a method for separating and detecting hemoglobin contents contained in blood and measuring the amount of the contents, and separation analysis by a general liquid chromatography method employing the system including a sample injection part, a sample separation part including a separation column, and a detection part is well known to a person skilled in the art. However, the scope of application of the device according to the present invention is not limited to this.

Note that the embodiment illustrated in the drawings is a mere example of the present invention, and the present invention of course includes not only the invention directly disclosed by the above-described embodiment but also various improvements and alterations to be done by a person skilled in the art within the scope of the present invention as claimed in the claims.

INDUSTRIAL APPLICABILITY

The sample injection device for biochemical analysis, the flow-type biochemical analysis device which uses the sample injection device, and the measurement method for hemoglobin components according to the present invention can be preferably used in various types of analyses and have high levels of industrial applicability.

REFERENCE SIGNS LIST

1 Carrier liquid tank
2 Carrier pump
3A, 3B Carrier-liquid channel
4 Sample injection device
5 Column
6 Detection unit
10 Housing
11 Sample injection part 12A Inlet-side channel
12B Outlet-side channel
13, 14 Septum (Septa)
15 Upper block
16 Locking nut
17 Guide hole
18 Cylindrical guide
19 Lower block
20 Locking nut
21 Annular space
22 Guide hole
23 Discharge pipe
24 Discharge path
25 Discharge pump (Waste pump)
26 Sample vessel
27 Needle
28 Needle moving unit
29 Measurement pump (Sampling pump)
30 Switching valve
31 Hemolysis-dilution-washing liquid tank

The invention claimed is:

1. A sample injection device for biochemical analysis configured to inject a sample into a carrier-liquid channel, the device comprising:
   a septum on a lower wall side at a sample injection position of the carrier-liquid channel;
   a septum on an upper wall side at the sample injection position of the carrier-liquid channel;
   a vessel which is arranged below the septum on the lower wall side and configured to store the sample;
   a cylindrical needle which is configured to penetrate through the septum on the upper wall side in a vertical direction and penetrate through the septum on the lower wall side;
   a cylindrical guide provided below the septum on the lower wall side and configured to guide the cylindrical needle;
   a needle moving unit configured to induce the cylindrical needle to move in a vertical direction and to induce the cylindrical needle to move at least to a sample drawing position, at which a tip of the cylindrical needle faces an inside of the vessel after having penetrated through the septum on the lower wall side, to a sample injection position, at which the tip of the cylindrical needle faces an inside of the carrier-liquid channel after having exited through the septum on the lower wall side, and to a washing position, which is set between the sample drawing position and the sample injection position and at which the tip of the cylindrical needle faces an inside of the cylindrical guide;
   a measurement pump connected with the cylindrical needle on a side of a base end section thereof and configured to carry out drawing when the cylindrical needle is positioned at the sample drawing position and carry out discharge when the cylindrical needle is positioned at the sample injection position;
   a pretreatment-, dilution-, or washing-liquid tank;
   a switching valve which is a three-way valve disposed between the base end section of the cylindrical needle, the measurement pump and the pretreatment-, dilution-, or washing-liquid tank and which connects the measurement pump with the pretreatment-, dilution-, or washing-liquid tank at a first position of the switching valve and connects the measurement pump with the base end section of the cylindrical needle at a second position of the switching valve; and
   a discharge pump connected to a space surrounding a tip of the cylindrical guide and configured to carry out drawing,
   wherein the measurement pump can draw liquid from the pretreatment-, dilution-, or washing-liquid tank at the first position of the switching valve and discharge the drawn liquid to the inside of the cylindrical needle at the second position of the switching valve, and
   wherein at the washing position, washing liquid having been discharged to the inside of the cylindrical needle by the measurement pump is discharged from the tip of the cylindrical needle and the washing liquid is drained by using the discharge pump.

2. The sample injection device for biochemical analysis according to claim 1, wherein at the sample drawing position, pretreatment or dilution liquid can be discharged from the tip of the cylindrical needle into the vessel.

3. A flow type biochemical analysis device comprising:
   the sample injection device according to claim 1; and
   a separation and detection unit provided in the carrier-liquid channel on a downstream side of the sample injection device and configured to separate and detect a content in the sample.

4. A measurement method for hemoglobin components the method comprising:
   injecting blood as the sample into the carrier-liquid channel with the sample injection device according to claim 1; and
   separating and detecting hemoglobin components contained in the blood and measuring an amount of the hemoglobin components.

* * * * *